United States Patent [19]

Snyder et al.

[11] 4,319,956

[45] Mar. 16, 1982

[54] NONWOVEN WEB MATERIAL FOR MEDICAL TOWELS AND THE LIKE

[75] Inventors: Charles E. Snyder, Enfield; Colin Elston, Windsor, both of Conn.

[73] Assignee: The Dexter Corporation, Windsor Locks, Conn.

[21] Appl. No.: 159,681

[22] Filed: Jun. 16, 1980

[51] Int. Cl.³ ............................................. D21H 3/44
[52] U.S. Cl. ................................ 162/146; 162/168 R; 428/288; 428/290; 128/296
[58] Field of Search ................... 162/146, 158, 168 R, 162/168 N, 168 NA, 169; 128/296, 292, 290 W; 428/288, 290; 260/29.6 ME, 29.6 E, 29.6 MQ, 29.6 MN

[56] References Cited

U.S. PATENT DOCUMENTS 3,922,462 11/1975 Katz et al. ............................ 428/290
4,007,083 2/1977 Ring et al. ............................ 162/158
4,172,173 10/1979 Trapasso et al. .................... 428/290

*Primary Examiner*—William F. Smith
*Attorney, Agent, or Firm*—Prutzman, Kalb, Chilton & Alix

[57] ABSTRACT

A new and improved, highly absorbent, nonwoven web material that exhibits a cytotoxicity level of zero is provided for use as a disposable medical towel and the like. The web material possesses a unique combination of physical properties, such as absorbent holding capacity equal to or greater than present commercially available products, rapid rewettability, high wet tensile strength, high delamination resistance and superior wet abrasion resistance. This unique material includes a water laid nonwoven base web saturated with an inherently hydrophobic latex binder containing up to 2 percent by weight of a polyol surfactant.

10 Claims, No Drawings

NONWOVEN WEB MATERIAL FOR MEDICAL TOWELS AND THE LIKE

The present invention relates generally to disposable medical towels and the like. More particularly it is concerned with a new and improved highly absorbent nonwoven, web material having particular application as a medical towel of the disposable type.

Nonwoven products used heretofore as disposable medical towels and the like have been formed as bonded dry laid sheets or wet laid material. Typical nonwoven products of the former type include skrim reinforced laminates, bonded carded webs and sprayed or print bonded air laid sheet material. These materials have exhibited good bulk and absorbent characteristics, namely, rapid rewettability and high holding capacity, for the intended end use but very poor wet properties such as wet tensile strength, wet abrasion resistance and wet delamination resistance. In fact it is a substantial disadvantage that particulate matter can easily be removed from the dry formed sheet material, particularly when it is in a wet condition. On the other hand, the wet laid nonwovens have typically exhibited superior wet characteristics such as wet tensile strength and wet abrasion and delamination resistance. Unfortunately the wet formed materials have exhibited relatively poor absorbent characteristics, such as rewettability and absorbent holding capacity. Of equal or greater importance is the fact that both types of nonwoven materials have heretofore exhibited an undesirably high cytotoxicity level; that is, the ability to have a toxic effect on living cells. The importance of this characteristic in applications such as medical towels is self evident.

Accordingly, it is an object of the present invention to provide a new and improved, highly absorbent, nonwoven disposable web material that exhibits a cytotoxicity test level of zero and is well suited for use as a medical towel and the like. More particularly, the present invention provides a new and improved nonwoven material of the type described that exhibits excellent absorbent characteristics coupled with the desired wet properties. The material possesses a unique combination of physical properties, such as absorbent holding capacity equal to or greater than present commercially available products, rapid rewettability, high wet tensile strength, high delamination resistance and superior wet abrasion resistance, all while successfully passing the cytotoxicity test with a score of zero. This unique fibrous web material exhibits the aforementioned characteristics by treating a nonwoven base web material with a latex bonding system selected so as to assure the requisite zero cytotoxicity level and other desired characteristics.

Other objects will be in part obvious and in part pointed out more in detail hereinafter.

A better understanding of the objects, advantages, features, properties and relationships of the invention will be obtained from the following detailed description that sets forth illustrative embodiments and is indicative of the way in which the principles of the invention are employed.

Although the invention is believed to have application to all nonwoven fibrous web materials, for clarity of illustration and ease of understanding it will be described hereinafter in connection with the manufacture of wet laid non-woven fibrous webs. The advantages achieved in accordance with the present invention are obtained by providing a fibrous nonwoven web material wherein the fibers are disposed in a random three-dimensional network as a relatively bulky lightweight water laid material. Initially the fibers are retained as an integral sheet or web structure by both the physical interengagement between the fibers and the light bonding factor achieved through hydrogen bonding as the wet laid web material is formed.

The preformed and binderless fibrous web material is dried and then is treated in accordance with the present invention with a particular latex binding system. The binder is preferably incorporated into the sheet material in a size press or other suitable applicating device that will assure saturation and controlled pick-up of the binder by the web material.

In carrying out the present invention a fibrous base paper is initially produced in the form of a continuous web material in accordance with known and conventional papermaking techniques. The nonwoven fibrous base web used to produce the materials of the present invention that exhibit the improved properties, characteristics, and uses set forth therein is made by a wet papermaking process that involves the general steps of forming a fluid dispersion of the requisite fibers and depositing the dispersed fibers on a fiber collecting wire in the form of a continuous sheet like web material. The fiber dispersion may be formed in a conventional manner using water as the dispersant or by employing other suitable fluid dispersing media. Preferably, aqueous dispersions are employed in accordance with known papermaking techniques and accordingly the fiber dispersion is formed as a dilute aqueous suspension or furnish of papermaking fibers. The fiber furnish is then conveyed to the web forming screen or wire, such as a Fourdrinier wire, of a papermaking machine and the fibers are deposited on the wire to form a fibrous base web or sheet that is subsequently dried in a conventional manner. The base sheet or web thus formed may be treated either before, during, or after the complete drying operation with the desired latex treating solution used in accordance with the present invention but in the preferred embodiment is treated subsequent to drying.

Although substantially all commercial papermaking machines, including rotary cylinder machines may be used, it is desirable where very dilute fiber furnishes are employed to use an inclined fiber collecting wire, such as that described in U.S. Pat. No. 2,045,095 issued to Fay H. Osborne on June 23, 1936. The fibers flowing from the headbox are retained on the wire in a random, three-dimensional network or configuration with slight orientation in the machine direction while the aqueous dispersant quickly passes through the wire and is rapidly and effectively removed.

Typically the fiber furnish used in the papermaking operation is adjusted in order to achieve the desired properties in the resultant end product. Since the preferred end use of the material produced in accordance with the present invention is for medical towels and the like exhibiting good absorbent characteristics, it is preferred that the sheet material of the present invention have high bulk and porosity properties. To achieve this, the fiber furnish incorporates a high alphacellulose pulp as about one quarter of the total fiber content. Pulps of this type are produced by reducing the hemicellulose content of the pulp through alkaline refining operations. While the high alphacellulose pulps are preferred since they produce the best results, other bulk imparting fibers having equivalent bulk imparting characteristics also can be employed.

As mentioned hereinbefore, absorbent characteristics alone are inadequate and appropriate wet properties including tensile strength are also desired. The use of high alphacellulose (low hemicellulose) pulps leads to webs of poor uniformity of fiber distribution and a substantial reduction in strength. Accordingly, conventional papermaking pulps have been preferred for webs requiring good strength characteristics. Therefore the stock or fiber furnish used to provide the new and improved properties of the present invention is a blend of fibrous materials that individually contribute to the desired end result. The blend preferably includes four different fibrous components: high alphacellulose pulps, hemicellulose wood pulps, hemp or hemplike vegetable fibers and synthetic fibers. A typical example of a fiber furnish composition used in accordance with the present invention in producing the new and improved absorbent medical towel is set forth in Table 1.

TABLE I

| Fiber Type | Specific Percentage | Percentage Range |
|---|---|---|
| High alphacellulose | 25 | 10–40 |
| Hemicellulose pulp | 25 | 10–30 |
| Hemp | 20 | 5–25 |
| Synthetic | 30 | 20–35 |

As is apparent from Table 1, one portion of the fiber furnish is made up of a conventional papermaking wood pulp (hemicellulose pulp) produced by the well known bleached Kraft process. These natural low alphacellulose fibers are of conventional papermaking length and have the advantage of retaining hemicellulose that contributes strength to the fibrous nonwoven structure. In accordance with the present invention, the amount of wood or Kraft fibers used in the fiber furnish can vary substantially depending upon the other components of the system. However, as indicated in the table the preferred amount is about 25 percent by weight and may vary 5–10 percent or more above or below the preferred amount. The amount used should, of course, be sufficient to contribute to the integrity and strength of the web particularly after treatment with the bonding system. Additionally, in order to provide improved strength characteristic it is preferred in accordance with the present invention to use a high cedar containing bleached Kraft pulp such as the pulp sold under the trademark "Crofton ECH" to obtain the benefits of those particular fibers.

As mentioned, the fiber furnish used in accordance with the present invention is an admixture of fibers of various types and lengths. Included in this blend are synthetic fibers that contribute to the wet mullen of the web and help carry the web at the wet end of the papermaking machine. Therefore, fibers such as viscose or acetate rayon are preferably included within the fiber furnish composition in the amounts shown in Table 1, hereinbefore. The fibers are preferably of a low denier of about 1.5–6 dpf. Generally the lower denier materials are of slightly shorter length than the higher denier in view of their tendency to entangle prior to deposition on the web forming screen. For example, 3 dbf rayon fibers can be used at lengths of about 12 mm while it is preferred to use a 1.5 dbp rayon fiber at a length of about 8 mm. As will be appreciated, longer fibers may be used where desired so long as they can be readily dispersed within the aqueous slurry of the other fibers.

Although the amount of rayon fibers used in the furnish may also vary depending upon the other components, it is generally preferred that the above indicated 20–35 percent by weight and preferably 30 percent by weight be used in most cases.

In addition to the conventional papermaking fibers of bleached Kraft and synthetic fibers such as rayon, the furnish of the present invention includes two different types of natural fibers that uniquely combine to provide the desired absorbency, bulk and other absorbent and wet properties sought in medical towels of the type described. As mentioned, some strength is imparted by the Kraft fibers, however, additional strength and absorbency is imparted in accordance with the present invention by including long vegetable fibers and particularly extremely long natural unbeaten fibers such as sisal, hemp, caroa, flax, jute and Indian hemp. These very long, natural fibers supplement the strength characteristics provided by the bleached Kraft and at the same time, provide a limited degree of bulk and absorbency coupled with a natural toughness and burst strength. Accordingly, the long vegetable fibers may be deleted entirely or used in varying amounts up to, for example, about 25 percent by weight. Generally the inclusion of such fibers is preferred but the total amount thereof is kept at about 20 percent in order to achieve the proper balance of desired properties in the end product.

Using a conventional papermaking technique, the fibers are dispersed at a fiber concentration within the range of 0.5 to 0.005 percent by weight and are preferably used at a fiber concentration of about 0.2 to 0.02 percent by weight. As will be appreciated papermaking aids such as dispersants and wet strength additives can be incorporated into the fiber slurry prior to web formation to assist in web formation and handling. These materials may constitute up to about 1 percent of the total solids within the fiber furnish and facilitate uniform fiber deposition, while providing the web with sufficient integrity so that it will be capable of undergoing subsequent resin treatment. These include natural materials such as guar gum, karaya gum, and the like as well as synthetic resin additives. However, all additives that are used in the fiber furnish should be of a nature that will result in a zero level of cytotoxicity.

As described hereinbefore the dilute aqueous fiber furnish is fed to the headbox of a papermaking machine and then to the fiber collecting wire where the fibers are deposited to form a continuous web or sheet. Preferably the base web material is dried immediately after web formation in a conventional manner by passing the newly formed material over a number of heated drum driers. This drying operation will permit controlled handling of the material during the subsequent resin treating operation.

The base web thus formed is subsequently saturated with the latex binder system utilized in accordance with the present invention. As will be appreciated the latex binding system must not only impart improved wet properties to the web, but also permit a high degree of absorbent characteristics within the final product including a relatively high or rapid rewettability character. Although hydrophilic binder systems normally might be expected to provide the requisite characteristics, this is not the case in the present invention. While hydrophilic binders are designed specifically for rewettable applications and will provide good rewettability, they usually result in poor holding capacity and a high level of cytotoxicity. Additionally webs so treated exhibit low wet tensile strength. Hydrophobic latex systems, on the other hand, normally cause the nonwoven materials to be extremely difficult to rewet.

In accordance with the present invention it has been found that a modified hydrophobic latex binder system will provide all of the desired characteristics in a unique and unusual fashion. The basic latex binder system is preferably an inherently hydrophobic and crosslinkable material which, in its unmodified condition, would result in poor wettability. More importantly, however, the basic hydrophobic material must be of a nature that will result in a zero level of cytotoxicity since this is an essential feature of the invention. Typically such binder systems have an extremely small amount of surfactant or even a complete absence of surfactants. Thus while a large number of hydrophobic latices will impart one or more of the desired characteristics of high wet abrasion resistance, delamination resistance and tensile strength, only a few acrylic and vinyl ethylene latices have been found to exhibit the requisite zero level in the cytotoxicity test. These have included materials such as the ethyl acrylate latex emulsions manufactured by B. F. Goodrich Chemical Co. and sold under the trademark "Hycar", the vinyl ethylene latex manufactured by Air Products Company and sold under the designation "402", and the acrylic latex system manufactured by Rohm and Haas Company, and designated "E 940". Other latices tested, even of an acrylic type have been found to exhibit a high cytotoxicity level or have failed from the standpoint of yielding poor wet physical properties or low absorbent holding capacity in the final end product. Since the vinyl ethylene latex is non-crosslinkable it gives poor strength characteristics and therefore is not used despite its zero cytotoxicity score. For this reason the base system found to give consistently acceptable results is the internally stabilized, crosslinkable acrylic latex binder system manufactured by B. F. Goodrich under the trademark "Hycar 2600×120". This material is believed to be a latex with an ethylacrylate base. When applied to the base web material as described hereinbefore, it results in a product having a zero cytotoxicity level. However, in its unmodified condition as received from the manufacturer it exhibits extreme difficulty in rewetting and must be modified by the incorporation therein of a selected surfactant at a controlled surfactant concentration level.

As mentioned the latex binder system used in accordance with the present invention is applied to the sheet material so as to saturate the sheet material and provide the requisite solid latex pick-up to provide the desired properties in the resultant web material. In this connection it has been found that saturation by size press or by similar operation will provide the desired result. The concentration of solid within the treating material may be varied so that the total latex solid pick-up of the sheet material is above 5 percent and less than 50 percent. However for most medical towel applications the latex pick-up preferably is between 10 and 30 percent with the preferred range being 15 to 25 percent by weight based on the total weight of the sheet material after being treated by the latex binder system.

The selected surfactant added to the latex must be capable of providing the desired rewetting characteristics without destroying the zero cytotoxicity level in the treated web material. Thus it is necessary to use a surfactant that will fulfill the characteristics of exhibiting a zero cytotoxic level and at the same time be effective as a rewetting agent in the inherently hydrophobic latex system. While a number of surfactants have been screened for these characteristics, only a few have been found to produce the desired results. In this connection the preferred materials are the nonionic polyol condensation products sold by BASF Wyandotte under the trademark "Pluronic". These condensation products are formed using hydrophobic bases that are condensation products of propylene oxide with propylene glycol. These hydrophobic bases are, in turn, reacted with ethylene oxide to provide the requisite polyol. Other surfactants that have shown a zero cytotoxic score are the materials sold under the trademark "Tween" by Imperial Chemical Industries. These are polyoxyethylene sorbitan monolaurate or sorbitan monopalmitate materials. However the "Pluronic" polyol materials have been found to provide substantially better rewetting characteristics than the "Tween" materials when used with the preferred acrylic latex system. Even among the polyol surfactant materials, it has been found that the higher molecular weight materials designated "L122" and "P123" (molecular weight approximately 5,000) are preferred, particularly when used at higher concentration levels. When lower concentrations are used, the lower molecular weight materials such as "Pluronic P103" may be employed without encountering a cytotoxicity problem.

The concentration level of the surfactant is maintained at about or less than 2 percent based on the solids within the latex system, with the preferred range of surfactant being about 1-2 percent. It will of course be appreciated that the specific amount of surfactant employed must be adequate to provide the desired wetting characteristics without destroying the zero cytotoxicity level of the nonwoven material treated with the surfactant modified latex system.

The cytotoxicity test procedure used to test the materials of the present invention is a standardized procedure that is a modification of the procedure described by Wilsnack et al "Human Cell Culture Toxicity of Medical Devices and Correlation to Animal Test", Biomat. Dev. Art. Org. 1(3), 543–562, (1973). In this procedure, a test sample of the substance under investigation and a control substance are exposed directly to eucaryotic cells in monolayer cultures. The culture medium is Eagle's Minimum Essential Medium supplemented with 10 percent Fetal Calf Serum, penicilin (100 units/ml) and streptomycin (100 mg/ml). The medium and the test samples are placed in duplicate test cells and incubated in a moist atmosphere of 95 percent air and 5 percent carbon dioxide at 37° C. for 24 hours. After the 24 hour incubation period, cultures are prepared for microscopic assessment of the cytotoxicity in accordance with the standard test procedure mentioned hereinbefore, and the resultant cultures are stained using a Harris Hematoxylin stain. Each culture is examined at 40× and 100× magnification for morphological signs of cytotoxicity such as lysis, vacuole formation and nuclear abnormalities. Each culture is scored on a relative scale from zero to four as follows: zero for no sign of cytotoxicity, 1 for toxic signs in less than 25 percent of the cells, 2 for toxic signs in 26–50 percent of the cells, 3 for toxic signs in 51–75 percent of the cells, and 4 for toxic signs in 76–100 percent of the cells.

The properties of the resultant web material after treated with the modified hydrophobic latex will vary depending on the amount of latex in the sheet. Thus the wet tensile strength of the material will improve as the amount of latex increases while the water holding capacity of the material decreases as the amount of latex increases. Accordingly there is a balancing of desired properties at the various concentration levels of the latex within the base web material. Generally the wet tensile strength of the material should exceed 500 g/25 mm and preferably should be at least 600 g/25 mm for light weight material (basis weight of about 35 gsm) and at least 900 g/25 mm for heavy weight material (basis weight about 65 gsm). On the other hand, the water holding capacity of the sheet material should be as high as possible and it is generally preferred that the water holding capacity exceed 300 percent and preferably be in the range of about 400 to 600 percent or more. A latex pick-up of about 20 percent by weight will generally provide the desired balance of properties.

It has also been found that the basis weight of the nonwoven web material will have an effect on its absorbency rate. Normally the lighter weight materials are used in a laminated construction while the heavier weight materials are used without combining them with other sheet materials. The lighter weight materials, namely those having a basis weight in the range of about 30–40 grams per square meter, should have an absorbency rate of less than 5 seconds while the bulkier, heavier weight materials falling within the basis weight range of about 60–90 grams per square meter will have a maximum absorbency rate of about 2 seconds. The absorbency rate is, of course, also effected by the level of the surfactant within the latex system with a one percent latex level typically providing an absorbency rate of 1 second while the higher latex level of 2 percent reduces the absorbency rate to about 0.5 seconds.

Not only should the wet strength be as high as possible commensurate with the desired holding capacity but the linting and delamination tendency should be low. The wet abrasion loss is one measure of these characteristics. Thus the web materials produced in accordance with the present invention and treated with the modified hydrophobic latex described hereinbefore should achieve a wet abrasion loss well below the 40–50 percent level and typically falling within the range of 10 to 30 percent and preferably is about 10–15 percent.

The following examples are given for purposes of illustration only in order that the present invention may be more fully understood. These examples are not intended to in any way limit the practice of the invention. Unless otherwise specified, all parts are given by weight.

EXAMPLE ONE

A fiber furnish was prepared from 25 percent high alpha cellulose Kraft soft wood pulp sold under the name "Buckeye HPZ", 25 percent high cedar containing bleached Kraft pulp sold under the name "Crofton ECH", 20 percent sisal pulp and 30 percent rayon fibers of 1.5 dpf and 8 mm in length. Using an inclined wire papermaking machine, bulky nonwoven web material was formed at different basis weights. After drying, the sheets were then saturation bonded in a size press with a modified hydrophobic latex bonding system to provide a latex pick-up of 20 percent. The bonding system consisted of a hydrophobic ethyl acrylate latex sold under the trade name "HYCAR 2600×120" which had been modified with the addition of 2 percent, based on the latex solids, of the surfactant "Pluronic P103". The physical properties of the resultant products are set forth in Table 2 as Samples 1a and 1b and are compared with two commercial products designated Commercial K for a scrim reinforced nonwoven drylaid material and Commercial F for a drylaid saturation bonded material. As can be seen the web materials of this Example compare favorably with the commercial products yet exhibit a zero cytotoxicity level and lower abrasion loss coupled with excellent holding capacity.

TABLE 2

| Properties | Units | Sample 1a | Commercial F | Sample 1b | Commercial K |
|---|---|---|---|---|---|
| Basis weight | gsm | 38 | 35 | 65 | 85 |
| Absorbent holding capacity | % | 480 | 380 | 500 | 260 |
| Absorbency rate | secs. | 3 | 3 | 1 | 3 |
| Avg. wet tensile | g/25mm | 830 | 615 | 1250 | 2000 |
| Wet abrasion loss | % | 15 | 32 | 16 | 89 |
| Cytotoxic score | | 0 | 4 | 0 | 4 |

EXAMPLE TWO

This example will show the effect of changes in the fiber blend of the base web material on the performance characteristics of the absorbent medical towel material.

The procedure of Example One was followed in preparing three fiber furnishes. The first fiber furnish was identical to the furnish of Example One while in the remaining two furnishes only the amount of bleached Kraft pulp remained unchanged. The specific amounts of each fibrous component are set forth in Table 3 which shows the variation in the fiber furnish and the resultant differences in the absorbent capacity and wet tensile strength of the resultant material. In this example Pluronic P122 was used in place of the surfactant of Example One at the same concentration and the latex pick-up was 20 percent.

TABLE 3

| Furnish Components | Units | Sample 2a | Sample 2b | Sample 2c |
|---|---|---|---|---|
| ECH Kraft | % | 25 | 25 | 25 |
| HPZ Pulp | % | 25 | 35 | 35 |
| Sisal 571 | % | 20 | 20 | 10 |
| Rayon 1.5 × 8mm | % | 30 | 20 | 30 |
| Basis weight | gsm | 65 | 65 | 65 |
| Absorbent capacity | % | 440 | 404 | 421 |
| Wet tensile | g/25 mm | 1220 | 1990 | 1450 |
| Cytotoxic score | | 0 | 0 | 0 |

EXAMPLE THREE

This example illustrates how the amount of latex on the sheet material will influence the properties of the web material.

A base web material was prepared using the fiber furnish of Example One. The dried base web had a basis weight of 47.5 gsm. The latex was Hycar 2600×120 and the surfactant employed was Pluronic L122 at a concentration level of 2 percent based on the latex solids. The concentration of solids in the latex was adjusted to vary the pick-up as the webs were saturated in a size press. The effect at different latex pick-up levels is reported in Table 4.

TABLE 4

| Latex Pick-up (%) | Wet Tensile (g/25 mm) | Water Holding Capacity (%) |
|---|---|---|
| 0 | 182.8 | 712.6 |

TABLE 4-continued

| Latex Pick-up (%) | Wet Tensile (g/25 mm) | Water Holding Capacity (%) |
|---|---|---|
| 5.35 | 699.7 | 546.5 |
| 10.0 | 1098.8 | 496.9 |
| 21.8 | 1594.1 | 415.1 |
| 31.4 | 2277.9 | 369.8 |
| 40.2 | 2787.9 | 293.4 |
| 45.5 | 2361.6 | 268.4 |

EXAMPLE FOUR

This example illustrates the effect of sterilization by steam or ethylene oxide.

The procedure of Example One was repeated except that samples of the products were sterilized after being produced and the resultant properties are reported in Table 5. The cytotoxicity score of 1 for the ethylene oxide sterilized material is believed to be due to residual ethylene oxide in the sheet material.

TABLE 5

| Properties | Units | Un-Sterilized | Steam Sterilized | ETO Sterilized |
|---|---|---|---|---|
| Basis weight | gsm | 62.7 | 65.2 | 62.7 |
| Dry tensile | g/25mm | 3600 | 3475 | 4035 |
| Wet tensile | g/25mm | 1165 | 1235 | 1265 |
| Absorbent capacity | % | 432 | 429 | 441 |
| Inclined absorbency | mm | 145 | 164 | 147 |
| Penetration time | sec. | .8 | .75 | .8 |
| Wet abrasion loss | % | 19.6 | 10.0 | 11.5 |
| Cytotoxicity | | 0 | 0 | 1 |
| Primary skin irritation | | 0 | — | 0 |

As will be apparent to persons skilled in the art, various modifications, adaptations and variations of the foregoing specific disclosure can be made without departing from the teachings of the present invention.

We claim:

1. A bonded fibrous web material well suited for use as a single use disposable medical towel and exhibiting rapid rewettability coupled with high wet abrasion resistance comprising a fibrous nonwoven web material saturation bonded with a hydrophobic latex, said bonded web having a web abrasion loss of less than about 40 percent, an absorbent holding capacity in excess of 300 percent, an absorbency rate of less than 5 seconds and a cytotoxicity level of zero, said hydrophobic latex being an internally stabilized emulsion of a crosslinkable acrylic binder and containing up to 2 percent by weight based on the solids within the latex of a nonionic, polyol surfactant having a cytotoxicity level of zero at said concentration.

2. The web material of claim 1 wherein the web material containing more than 5 percent and less than 50 percent by weight of the acrylic binder.

3. The web material of claim 1 wherein the surfactant is a nonionic condensation product of ethylene oxide and a hydrophobic base.

4. The web material of claims 1, 2 or 3 wherein the fibrous nonwoven web is comprised of a blend of natural and synthetic fibers in the form of a wet laid web material.

5. The web material of claims 1, 2 or 3 wherein the fibrous nonwoven web is comprised of 10-40 percent by weight high alpha cellulose pulp, 10-30 percent by weight hemi cellulose pulp, 5-25 percent by weight vegetable fiber and 20-35 percent by weight of synthetic fiber.

6. The web material of claim 2 wherein the acrylic binder has an ethyl acrylate base and the web material contains 10-30 percent by weight of binder.

7. The web material of claim 3 wherein the hydrophobic base is a reaction product of propylene oxide and propylene glycol.

8. The web material of claims 3 or 7 wherein the surfactant has a molecular weight of about 5,000.

9. The web material of claim 1 wherein the latex is an internally stabilized acrylic emulsion modified with a nonionic surfactant at a concentration of 1-2 percent by weight based on the solids in the latex, said web exhibiting a wet tensile strength of at least about 600 g/25 mm., an absorbent holding capacity of at least about 400 percent, an absorbency rate of less than 2 seconds and wet abrasion loss of less than about 30 percent.

10. The web material of claim 9 wherein the acrylic emulsion is made from ethyl acrylate and the nonionic surfactant is a polyol condensation product of ethylene oxide and a hydrophobic base obtained from the reaction of propylene oxide and propylene glycol.

* * * * *